(12) United States Patent
Shi

(10) Patent No.: US 11,350,947 B2
(45) Date of Patent: Jun. 7, 2022

(54) LIGATION DEVICE, UNLOCKING METHOD AND LIGATION INSTRUMENT

(71) Applicant: HANGZHOU AGS MEDTECH CO., LTD., Zhejiang (CN)

(72) Inventor: Baiming Shi, Hangzhou (CN)

(73) Assignee: HANGZHOU AGS MEDTECH CO., LTD., Hangzhou (CN)

( * ) Notice: Subject to any disclaimer, the term of this patent is extended or adjusted under 35 U.S.C. 154(b) by 183 days.

(21) Appl. No.: 16/714,855

(22) Filed: Dec. 16, 2019

(65) Prior Publication Data

US 2020/0113573 A1    Apr. 16, 2020

Related U.S. Application Data

(63) Continuation of application No. PCT/CN2017/088732, filed on Jun. 16, 2017.

(51) Int. Cl.
*A61B 17/128*     (2006.01)
*A61B 17/122*     (2006.01)
(Continued)

(52) U.S. Cl.
CPC ........ *A61B 17/1285* (2013.01); *A61B 17/122* (2013.01); *A61B 2017/00358* (2013.01);
(Continued)

(58) Field of Classification Search
CPC ... A61B 17/12; A61B 17/122; A61B 17/1227; A61B 17/128; A61B 17/1285; A61B 2017/12004
See application file for complete search history.

(56) References Cited

U.S. PATENT DOCUMENTS 3,958,576 A * 5/1976 Komiya ............... A61B 17/083
                                                                606/142
8,444,660 B2 * 5/2013 Adams ................. A61B 17/122
                                                                606/157
(Continued)

FOREIGN PATENT DOCUMENTS

CN     104546055 A     4/2015
CN     204909551 U    12/2015
CN     106491176 A     3/2017

OTHER PUBLICATIONS

International Search Report in PCT/CN2017/088732 dated Mar. 20, 2018, 6 Pages.
(Continued)

*Primary Examiner* — Ryan J. Severson
(74) *Attorney, Agent, or Firm* — Metis IP LLC

(57) ABSTRACT

The present disclosure relates to a ligation device, an unlocking method, and a ligation instrument. The ligation device may include a clip and a limiting tube. A distal end of the clip may be used for ligation. The limiting tube may be provided with an accommodation channel, and a proximal end of the clip may be connected with the accommodation channel, and the proximal end of the clip may move into or out of the limiting tube. The clip may be provided with a locking portion, and the limiting tube may be provided with a locking position that is matched with the locking position. When the locking portion is locked with the locking position, the locking portion may be unlocked from the locking position by operating the locking portion. Alternatively, the clip may be provided with an unlocking portion that is coupled with the locking portion. The locking portion may be unlocked from the locking position by operating the unlocking portion. The ligation device may be re-opened after being locked for ligation, causing no secondary damage to the ligated tissue.

19 Claims, 17 Drawing Sheets

(51) Int. Cl.
*A61B 90/00* (2016.01)
*A61B 17/00* (2006.01)
*A61B 17/12* (2006.01)

(52) U.S. Cl.
CPC ............. *A61B 2017/12004* (2013.01); *A61B 2090/034* (2016.02)

(56) References Cited

U.S. PATENT DOCUMENTS

| | | | | |
|---|---|---|---|---|
| 8,663,247 | B2* | 3/2014 | Menn | A61B 17/1285 |
| | | | | 606/142 |
| 8,685,048 | B2* | 4/2014 | Adams | A61B 17/122 |
| | | | | 606/157 |
| 8,709,027 | B2* | 4/2014 | Adams | A61B 17/1227 |
| | | | | 606/157 |
| 9,072,520 | B2* | 7/2015 | Terada | A61B 17/1227 |
| 9,138,234 | B2* | 9/2015 | Li | A61B 17/122 |
| 9,271,731 | B2* | 3/2016 | Adams | A61B 17/122 |
| 9,332,988 | B2* | 5/2016 | Adams | A61B 17/083 |
| 9,795,390 | B2* | 10/2017 | Jin | A61B 17/1285 |
| 10,143,479 | B2* | 12/2018 | Adams | A61B 17/1285 |
| 10,172,623 | B2* | 1/2019 | Adams | A61B 17/1285 |
| 10,172,624 | B2* | 1/2019 | Adams | A61B 17/122 |
| 10,470,775 | B2* | 11/2019 | Shi | A61B 17/1227 |
| 10,610,237 | B2* | 4/2020 | Estevez | A61B 17/122 |
| 10,952,743 | B2* | 3/2021 | Adams | A61B 17/1285 |
| 2010/0152753 | A1* | 6/2010 | Menn | A61B 17/00234 |
| | | | | 606/158 |
| 2011/0238093 | A1* | 9/2011 | Matsuoka | A61B 17/1285 |
| | | | | 606/151 |
| 2013/0072945 | A1 | 3/2013 | Terada | |
| 2013/0123818 | A1* | 5/2013 | Li | A61B 17/122 |
| | | | | 606/157 |
| 2014/0135801 | A1* | 5/2014 | Menn | A61B 17/083 |
| | | | | 606/142 |
| 2016/0242778 | A1 | 8/2016 | Xu et al. | |
| 2016/0367258 | A1 | 12/2016 | Jin et al. | |
| 2018/0344323 | A1* | 12/2018 | Shi | A61B 17/122 |
| 2019/0357974 | A1* | 11/2019 | Shi | A61B 90/361 |
| 2020/0008811 | A1 | 1/2020 | Itoh et al. | |
| 2020/0060685 | A1* | 2/2020 | Han | A61B 17/1285 |
| 2020/0113573 | A1* | 4/2020 | Shi | A61B 17/122 |

OTHER PUBLICATIONS

Written Opinion in PCT/CN2017/088732 dated Mar. 20, 2018, 7 Pages.

* cited by examiner

LIGATION DEVICE, UNLOCKING METHOD AND LIGATION INSTRUMENT

CROSS-REFERENCE TO RELATED APPLICATIONS

The present application is a continuation application of International Application No. PCT/CN2017/088732, filed on Jun. 16, 2017, the entire contents of which are incorporated herein by reference.

TECHNICAL FIELD

The present disclosure relates to medical instruments, and more particularly, relates to a ligation device, an unlocking method, and a ligation instrument.

BACKGROUND

The stomach and intestines of the organism often bleeding due to various diseases, accidental injuries, or damage of endoscopic treatment. For active bleedings, hemostasis methods such as drug spraying, high-frequency electricity, laser, argon burning, hemostasis clip mechanical compression, and so on, are generally performed for treatment. The hemostasis clip mechanical compression is more reliable for the treatment of active bleeding caused by non-varicose veins, and has also been accepted by doctors and patients. The hemostasis clips can also close the mucosal damage of the digestive tract to promote the healing of the wound.

Once the traditional ligation device is locked, the locking cannot be removed without damage. The locking can only be destroyed by violent destruction, forcing the clamping part to be forcibly separated from the tissue, which may cause secondary damage to the tissue or re-bleeding.

According to application No. CN201520556321.X, the hemostatic clip can realize the functions such as repeated opening and closing, rotation, and so on, before the clip portion is closed and not released. However, when the clip portion of the hemostatic clip is clamped with the tissue and released, that is, the clip portion and the delivery portion are separated, the clip portion may clamp the tissue firmly. If the releasing position is not suitable or the releasing of the hemostatic clip is failed after the clip portion of the hemostatic clip is released, using other instruments to forcibly pull the clip from the clamped tissue may cause damage to the clamped tissue and surrounding tissues, which may even enlarge the original wound surface to cause more local damage. If the hemostatic clip is not removed, it may affect the hemostatic effect or subsequent endoscopic operation.

SUMMARY

In view of the above-mentioned facts, in order to overcome the defects of the prior arts, the present disclosure provides a ligation device, an unlocking method, and a ligation instrument. The ligation device may be re-opened after being locked for ligation, and cause no secondary damage to the ligated tissue.

Technical solutions of the present disclosure may include:

A ligation device may include a clip and a limiting tube. A distal end of the clip may be used for ligation. The limiting tube may be provided with an accommodation channel, and a proximal end of the clip may be accommodated within and movable relative to the accommodation channel. The clip may be provided with a locking portion, and the limiting tube may be provided with a locking position. The locking portion may be matched with the locking position. When the locking portion is locked with the locking position, the locking portion may be unlocked from the locking position by operating the locking portion. Alternatively, the clip may be provided with an unlocking portion that is coupled with the locking portion, and the locking portion may be unlocked from the locking position by operating the unlocking portion.

In some embodiments, the locking portion may be an elastic lock. When the elastic lock is locked with the locking position, the elastic lock may be locked with the locking position by bouncing outward from the accommodation channel.

In some embodiments, the clip may include two clip arms. The proximal ends of the two clip arms may be connected, and the proximal ends of the two clip arms may form a locking ring. The locking ring may include the locking portion. When the locking ring is locked with the locking position, two sides of the locking ring or one side of the locking ring may extend into the locking position.

In some embodiments, the clip arm may be provided with the unlocking portion, and the unlocking portion may be located at a proximal end or a distal end of the locking ring.

In some embodiments, the clip may include an elastic arm. The elastic arm may be provided with a locking convex. The locking convex may form the locking portion.

In some embodiments, the clip may include a clip arm. A proximal end of the clip arm may form the elastic arm.

In some embodiments, the elastic arm may be provided with the unlocking portion. The unlocking portion may be located at a proximal end or a distal end of the locking convex.

In some embodiments, a proximal end of the limiting tube may form the locking position. The locking portion may be locked with the proximal end of the limiting tube via buckling. Alternatively, the inner wall of the accommodation channel may be provided with a locking concave. The locking concave may form the locking position. The locking portion may extend into the locking concave such that the locking portion may be locked with the locking concave via buckling.

In some embodiments, a side wall of the limiting tube may be provided with a locking window. The locking window may form the locking position. When the locking portion is locked with the locking position, the locking portion may extend into the locking window. The locking portion may be unlocked from the locking window by operating the locking portion through the locking window.

In some embodiments, the unlocking position may be located at the vicinity of the proximal end of the limiting tube. When the locking portion is locked with the locking position, the unlocking portion may be located outside the proximal end of the accommodation channel. Alternatively, the side wall of the limiting tube may be provided with the unlocking window. When the locking ring is locked with the locking position, the unlocking window may correspond to the unlocking portion. The locking portion may be unlocked from the locking position by operating the locking portion through the locking window.

In some embodiments, the locking portion may be unlocked from the locking position by operating the locking portion through the locking position. Alternatively, the limiting tube may be provided with an unlocking position, and the locking portion may be unlocked from the locking position by operating the locking portion through the unlocking position.

In some embodiments, the proximal end of the clip may be movable relative to the limiting tube. When the clip is in the first position relative to the limiting tube, the distal end of the clip may be opened, and the locking portion and the locking position may be unlocked. When the clip is in the second position relative to the limiting tube, the distal end of the clip may be closed, and the locking portion may be locked with the locking position.

A ligation device may include a delivery portion and a ligation device. The delivery portion may include a sheath and a shaft. The sheath may be sleeved outside the shaft. The ligation device or the delivery portion may be further provided with a first releasing portion. The shaft may be connected with the clip through the first releasing portion, and the shaft may be operated to drive the clip to move relative to the limiting tube. When the shaft is pulled to a first releasing condition, the first releasing portion may separate the shaft from the clip.

An unlocking method for unlocking a ligation device. The method may include pressing the locking portion or the unlocking portion inwardly to unlock the locking portion from the locking position.

In some embodiments, the clip of a first ligation device may be closed, and the locking portion of the first ligation device may be locked with the locking position of the first ligation device. The clip of a second ligation device may be sleeved on the first ligation device, and the clip of the second ligation device may be closed to squeeze the locking portion or the unlocking portion of the first ligation device from inside to outside such that the locking portion of the first ligation device may be unlocked from the locking position of the first ligation device.

In some embodiments, the ligation device may be unlocked by using an unlocking clamp. The unlocking clamp may include a clamp arm, and an opening and closing device connected with the clamp arm. The unlocking clamp may be sleeved on the ligation device. The opening and closing device may be operated to close the clamp arm such that the clamp arm may press the locking portion or the unlocking portion inwardly to unlock the locking portion from the locking position.

In some embodiments, the ligation device may be unlocked by using an unlocking sleeve. The unlocking sleeve may include a snare, and a limiting device connected with the snare. The snare may be sleeved on the ligation device. The limiting device may be operated to tighten the snare such that the snare may press the locking portion or the unlocking portion inwardly to unlock the locking portion from the locking position.

The beneficial effects of the present disclosure may include:

1. The ligation device may include a clip and a limiting tube. A distal end of the clip may be used for ligation. The limiting tube may be provided with an accommodation channel, and a proximal end of the clip may be accommodated within and movable relative to the accommodation channel. The proximal end of the clip may move into or out of the limiting tube. The clip may be provided with a locking portion, and the limiting tube may be provided with a locking position. The locking portion may be matched with the locking position. When the locking portion is locked with the locking position, the locking portion may be unlocked from the locking position by operating the locking portion. Alternatively, the clip may be provided with an unlocking portion that is coupled with the locking portion, the locking portion may be unlocked from the locking position by operating the unlocking portion.

When ligating, the distal end of the clip may firstly be opened and clamp the tissue of the ligating portion. Then the clip may be moved to the proximal end to lock the locking portion with the locking position. At this time, the location of the clip in the limiting tube may be locked, and the clip cannot be released from the distal end of the accommodation channel. The clip may remain closed to ensure that the ligation is not released.

After ligating, if it is necessary to open the clip to release the ligated tissue, the locking portion or the unlocking portion may be operated (the unlocking portion is linked with the locking portion, and an operation on the unlocking portion may drive the locking portion to be unlocked) to unlock the locking portion from the locking position. At this time, the clip may be unlocked from the limiting tube, and the locking portion may re-enter into the accommodation channel. The clip may be moved from the second position to the first position, and the distal end of the clip may be re-opened to release the ligated tissue. During the process of releasing the ligated tissue, the ligated tissue may be simply released by the clip and not subjected to additional forces, which may not cause secondary damage to the tissue.

2. The locking portion may be an elastic lock. When the elastic lock is locked with the locking position, the elastic lock may be locked with the locking position by bouncing outward from the accommodation channel.

When ligating, the distal end of the clip may firstly be opened and clamp the tissue of the ligating portion. Then the clip may be moved to the proximal end. By using the cooperation of the locking portion and the accommodation channel of the limiting tube, when the clip is moved to a suitable position, the locking portion may automatically bounce outward and be locked with the locking position. At this time, the location of the clip in the limiting tube may be locked, and the clip cannot be released from the distal end of the accommodation channel. The clip may remain closed to ensure that the ligation is not released.

After ligating, if it is necessary to open the clip to release the ligated tissue, the locking portion or the unlocking portion may be pressed inward (the unlocking portion is linked with the locking portion, and an operation on the unlocking portion may drive the locking portion to be unlocked), so that the locking portion may be detached from the locking position and the locking portion may be unlocked from the locking position. At this time, the clip may be unlocked from the limiting tube, and the locking portion may be pressed to re-enter into the accommodation channel. The clip may be moved from the locked position to the distal end, and the distal end of the clip may be re-opened to release the ligated tissue. During the process of releasing the ligated tissue, the ligated tissue may be simply released by the clip and not subjected to additional forces, which may not cause secondary damage to the tissue.

As used herein, the "proximal end" and "distal end" may be referenced to the line in which the central axis of the accommodation channel is located. The direction toward the operator on the central axis may be referred to as the "proximate end", and the direction toward the ligated tissue on the central axis may be referred to as the "distal end". However, the line may also have a certain angle with the central axis, other than being completely along the central axis.

As described herein, the locking portion may be opened "outward" or pressed "inward". The outward may refer to a direction away from the central axis of the accommodation channel, and the inward may refer to a direction pointing to the central axis of the accommodation channel.

As described herein, the elasticity of the locking portion means that as long as the function that the locking portion can automatically bounce outward and be locked with the locking position is satisfied, any elastic material may be used, and is not limited herein. The locking portion may be made of an elastic material or a non-elastic material as needed. The locking portion may be integrally formed with the clip, or the locking portion and the clip may be formed separately and then joined together.

3. The clip may include two clip arms. The proximal ends of the two clip arms may be connected, and the proximal ends of the two clip arms may form a locking ring. The locking ring may include the locking portion. When the locking ring is locked with the locking position, two sides of the locking ring or one side of the locking ring may extend into the locking position.

The proximal end of the limiting tube may form the locking position. When the distal end of the clip is opened, the locking ring may be squeezed into the accommodation channel. When the clip is locked, the locking ring may be at least partially located outside the accommodation channel. The width of the locking ring may be larger than the width of the accommodation channel and the locking ring may abut against the proximal end of the limiting tube. The locking ring may be caught by the proximal end of the accommodation channel and cannot enter the accommodation channel. At this time, the positional relationship of the clip and the limiting tube may be locked, and the clip may remain ligating and not be opened. When the locking ring is pressed inward, the width of the locking ring may be smaller than the width of the accommodation channel. Then, the locking ring may be unlocked from the locking position, and the clip may release the ligated tissue. The locking ring may be locked by using the proximal end of the limiting tube, which is simple in the structure.

Alternatively, the side wall of the limiting tube may be provided with a locking window, and the locking window may form the locking position. When the distal end of the clip is opened, the locking ring may be squeezed into the accommodation channel. When the clip is locked, the locking ring may be clipped in the locking window. When the locking ring is pressed inward through the locking window, the locking ring may be detached from the locking window. The locking window may provide an operable window through which the locking ring may be squeezed and unlocked. The locking window may include one or two or more locking windows. Preferably, the locking window may include two locking windows which are respectively corresponding to the two sides of the locking ring, and the two sides of the locking ring may be clipped in the locking windows. The side of the locking ring may or may not extend out of the locking window.

Preferably, the clip arm may be further provided with the unlocking portion, and the unlocking portion may be located at a proximal end or a distal end of the locking ring. When the unlocking portion is located at the proximal end of the locking ring, the unlocking portion may also be annular. When the unlocking portion is located at the distal end of the locking ring, the side wall of the limiting tube may be provided with an unlocking window. The unlocking window may correspond to the unlocking portion, and the unlocking portion may be pressed through the unlocking window.

4. The clip may include an elastic arm. The elastic arm may be provided with a locking convex. The locking convex may form the locking portion.

The proximal end of the limiting tube may form the locking position. When the clip is at the second position, the elastic arm may bounce the locking convex outward, and the locking convex may be locked with the locking position. On this basis, when the locking convex is pressed inward, the locking convex may be detached from the locking position. The locking convex may be locked with the locking position by using the elastic arm to bounce the locking convex outward, and the proximal end of the limiting tube may be directly used as the locking position, which is simple in the structure.

Alternatively, the side wall of the limiting tube may be provided with a locking window, and the locking window may form the locking position. When the clip is at the second position, the elastic arm may bounce the locking convex outward, and the locking convex may extend into the locking window. On this basis, when the locking convex is pressed inward through the locking window, the locking convex may be detached from the locking window. The locking window may provide an operating space for unlocking the locking relationship between the locking convex and the locking position, so that the ligation can be unlocked and the unlocking of the ligation may not cause secondary damage to the ligated tissue. The locking convex may include one or two or more locking convex. The locking window may include one or two or more locking windows.

5. Preferably, the clip may include a clip arm. A proximal end of the clip arm may form the elastic arm. The elastic arm may be formed by using the clip itself, of which the structure is simple and convenient to manufacture.

Preferably, the clip arm may be further provided with an unlocking portion, and the unlocking portion may be located at a proximal end or a distal end of the locking convex. The locking convex may be driven to move while pressing the unlocking portion.

6. Preferably, the clip may include two clip arms. The clip may further include a connecting pin. Each of the clip arms may be provided with a connecting hole. The connecting pin may be disposed in the connecting holes. When the clip is at the second position, the clip arms may slidably bounce outward along the connecting pin, and the locking convex may be locked with the locking position. When the distal end of the clip arm clamps the tissue to form a ligation, the proximal end of the clamp arm may be locked with the locking position, which if is simple in the structure.

7. The side wall of the limiting tube may be provided with a locking window, and the locking window may form the locking position. When the clip is locked, the locking convex may extend into the locking window. When the locking convex is pressed inward through the locking window, the locking convex may be detached from the locking window. The locking window may be set to prevent the limiting tube from blocking the locking portion. An unlocking clamp, an unlocking sleeve, or other tools may press the locking portion through the locking window to unlock the locking portion from the locking position. At this time, the locking portion itself may form the unlocking portion.

8. The vicinity of the proximal end of the limiting tube may be the unlocking position. When the clip is locked, the unlocking portion may be located outside the proximal end of the accommodation channel. The unlocking portion may be directly exposed outside the accommodation channel, and the clip may be unlocked by directly operating the unlocking portion.

The side wall of the limiting tube may be provided with an unlocking window. When the clip is locked, the unlocking window may correspond to the unlocking portion. When the unlocking portion is pressed inward through the unlocking window, the locking portion may be unlocked from the locking position. The unlocking window may be set to prevent the limiting tube from blocking the unlocking portion. An unlocking clamp, an unlocking sleeve, or other tools may press the unlocking portion through the unlocking window to unlock the locking portion from the locking position.

9. A ligation device may include a delivery portion and a ligation device. The delivery portion may include a sheath and a shaft. The sheath may be sleeved outside the shaft. The ligation device or the delivery portion may be further provided with a first releasing portion. The shaft may be connected with the clip through the first releasing portion, and the shaft may be operated to drive the clip to move relative to the limiting tube.

In conjunction with the endoscope, the delivery portion may be used to transport the ligation device into the human body. The clip may be driven to move toward the proximal end by pulling the shaft toward the proximal end. The clip may be driven to move toward the distal end by pushing the shaft toward the distal end. The first position may be located at the distal side of the second position. The clip may be at the first position by operating the shaft, and the distal end of the clip is opened. The shaft is pulled toward the proximal end, and the clip may be moved toward the proximal end. The clip may be pressed by the limiting tube to close. Then, the clip may clamp the tissue firmly. When the clip is moved to the second position, the locking portion may be locked with the locking position, and the clip may maintain the ligated state.

When the shaft is pulled to a first releasing condition, the first releasing portion may separate the shaft from the clip.

Preferably, the ligation device or the delivery portion may further be provided with a second releasing portion, and the sheath may be connected with the limiting tube through the second releasing portion.

When the shaft is pulled to a second releasing condition, the second releasing portion may separate the sheath from the limiting tube. The first releasing condition and the second releasing condition may be selected as needed. The first releasing condition and the second releasing condition may or may not be associated with the first position and the second position, and may be selected as needed.

After the shaft is separated from the clip or the sheath is separated from the limiting tube, the ligation device may be retained in the human body to maintain the ligated state. If the ligation device described in the present disclosure is used, the clip and the ligation may be released by pressing the locking portion inward to unlock the locking portion from the locking position. The tissue may be released without secondary damage. Alternatively, when the clip has been ligated but the shaft has not been separated from the clip or the sheath has not been separated from the limiting tube, the locking portion may be unlocked from the locking position to release the clip as needed.

The first position described above is located at the distal side of the second position. While any appropriate position may be selected as the first position or the second position as needed, and the first position and the second position may be located at any position of the ligation device.

DESCRIPTION OF REFERENCE SIGNS 100, ligation device, 110, clip, 111, clip arm, 112, locking portion, 113, connecting pin, 114, first releasing piece, 115, connecting hole, 116, hook, 120, limiting tube, 121, U-shaped member, 122, locking position, 123, clamping hole, 124, clamping portion, 125, accommodation channel, 140, unlocking portion, 150, unlocking window, 200, delivery portion, 210, sheath, 220, shaft, 300, controlling portion, 400, tissue, 510, snare, 520, limiting device, 610, clamp arm, 620, opening and closing device.

DETAILED DESCRIPTION

The present disclosure will be further described in detail below, but the implementation of the present disclosure is not limited thereto.

Embodiment One

Figure 1:
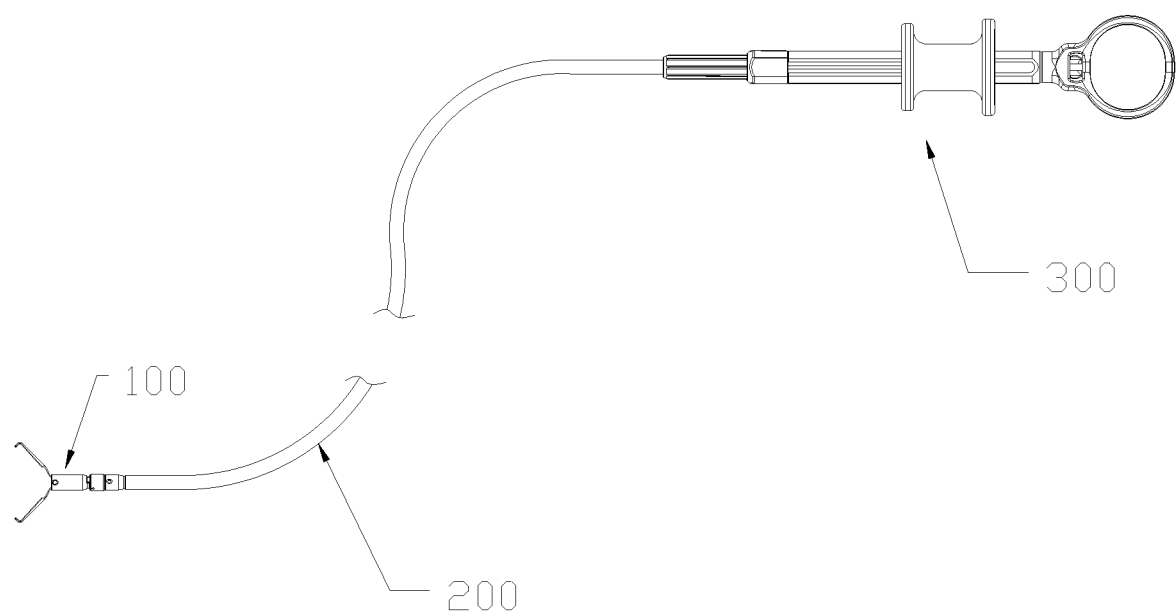
FIG. 1 is a schematic diagram illustrating an overall structure of a ligation device according to embodiment one of the present disclosure.

As shown in FIG. 1, a ligation instrument may include a ligation device 100, a delivery portion 200, and a controlling portion 300. The delivery portion 200 may include a sheath 210 and a shaft 220, and the sheath 210 may be sleeved on the shaft 220. The controlling portion 300 may be connected with the sheath 210 and the shaft 220. The controlling portion 300 may control the shaft 220 to move toward the proximal end or the distal end relative to the sheath 210. The ligation device 100 may include a clip 110 and a limiting tube 120. The clip 110 may further include a first releasing portion, and the limiting tube 120 may further include a second releasing portion. The shaft 220 may be connected with the clip 110 through the first releasing portion, and the sheath 210 may be connected with the limiting tube 120 through the second releasing portion. The operation of the shaft 220 may drive the clip 110 to a first position or a second position. When the shaft 220 is pulled to a first releasing condition, the first releasing portion may separate the shaft 220 from the clip 110. When the shaft 220 is pulled to a second releasing condition, the second releasing portion may separate the sheath 210 from the limiting tube 120.

Figure 13:
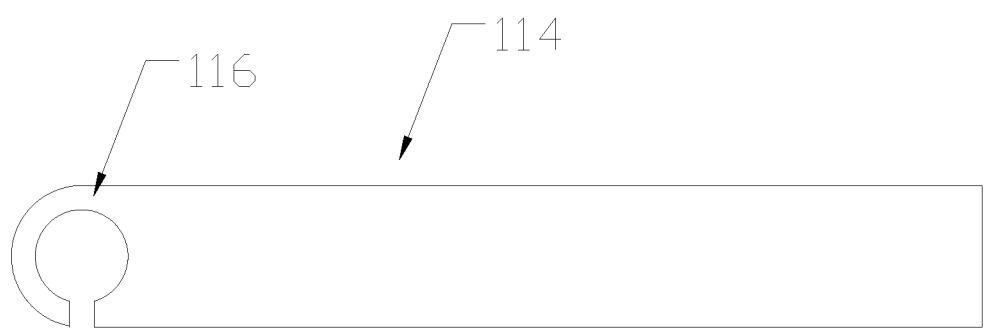
FIG. 13 is a schematic diagram illustrating a first releasing piece according to embodiment one of the present disclosure.
Figure 14:
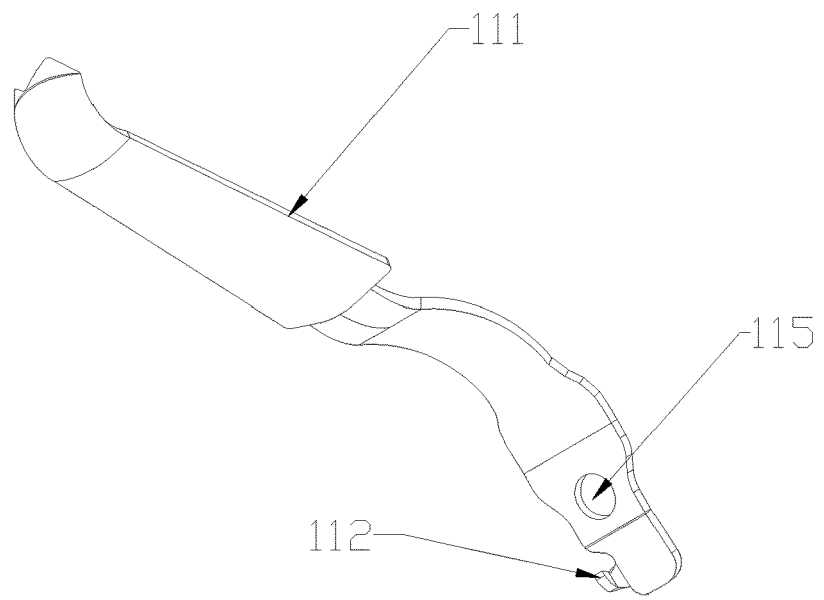
FIG. 14 is a schematic diagram illustrating a clip arm according to embodiment one of the present disclosure.

As shown in FIGS. 2 to 5, the clip 110 may include two clip arms 111 and a connecting pin 113. As shown in FIG. 14, the clip arm 111 may include a connecting hole 115, and the connecting pin 113 may be located in the connecting hole 115. The first releasing portion may include two first releasing pieces 114. As shown in FIG. 13, the proximal end of first releasing piece 114 may be connected with the shaft 220. The distal end of the first releasing piece 114 may be a deformable or broken hook 116, and the hook 116 may hook the connecting pin 113. In this embodiment, when the shaft 220 is pulled to a first releasing condition, the first releasing portion may separate the shaft 220 from the clip 110, which means pulling the shaft 220 to break or deform the first releasing piece 114, so that the first releasing piece 114 may be detached from the clip 110. But it is not limited to this embodiment, the first releasing portion may also include other structures cooperated with the corresponding first releasing condition.

Figure 6:
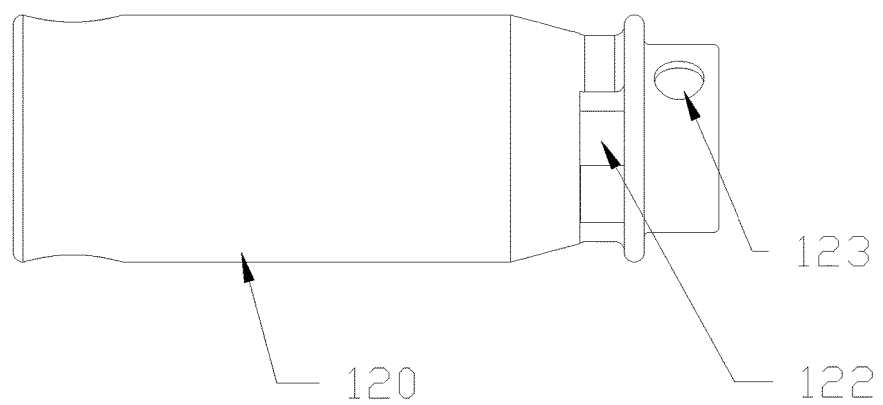
FIG. 6 is a schematic diagram illustrating a limiting tube according to embodiment one of the present disclosure.
Figure 7:
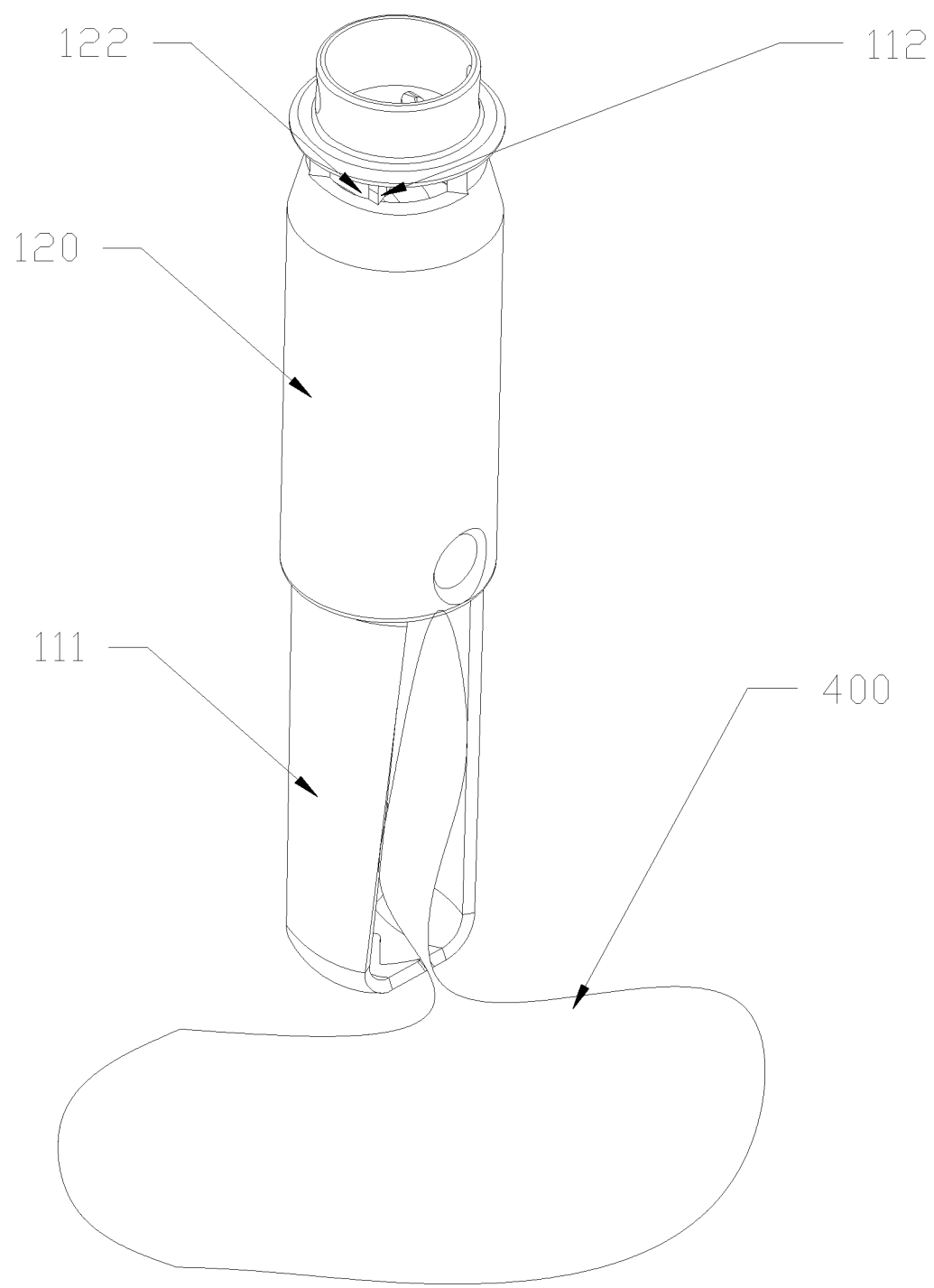
FIG. 7 is a second schematic diagram illustrating a ligation locking according to embodiment one of the present disclosure.
Figure 12:
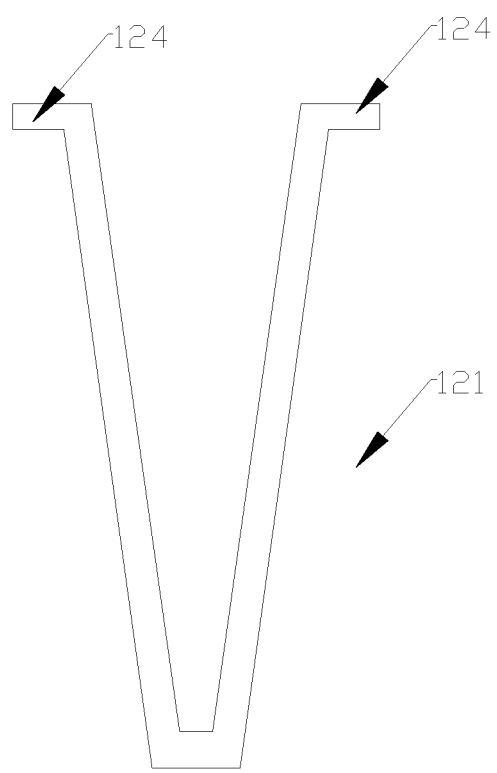
FIG. 12 is a schematic diagram illustrating a structure of a U-shaped piece according to embodiment one of the present disclosure.

As shown in FIG. 1, FIG. 6, and FIG. 7, a side wall of the limiting tube 120 may include a clamping hole 123. The distal end of the sheath 210 may include an opening corresponding to the clamping hole 123. The second releasing portion may include a U-shaped member 121. As shown in FIG. 12, each of the two ends of the U-shaped member 121 may include a clamping portion 124. The clamping portion 124 may pass through the clamping hole 123 and the opening of the sheath 210 such that the sheath 210 and the limiting tube 120 may be connected. In this embodiment, when the shaft 220 is pulled to a second releasing condition, the second releasing portion may separate the sheath 210 from the limiting tube 120, which means: due to the limit by the inner diameter of the accommodation channel 125, when the shaft 220 is pulled toward the proximal end to a certain position, the shaft 220 or other structure connected to the shaft 220 may be caught by the U-shaped member 121. If the shaft 220 is continuously pulled toward the proximal end, the U-shaped member 121 may be driven to move toward the proximal end. With the U-shaped member 121 moving toward the proximal end, the clamping portion 124 may be detached from the clamping hole 123 or the opening, and the sheath 210 may be separated from the limiting tube 120. But it is not limited to this embodiment, the second releasing portion may also include other structures cooperated with the corresponding second releasing condition.

As shown in FIGS. 2, 3, and 5-7, an inclined surface may be formed on the limiting tube 120 and at the vicinity of the locking position 122 (e.g., at the entrance of the locking position 122). The inclined surface may incline toward the center of the limiting tube 120 along the distal direction. In some embodiments, the inclined surface of the limiting tube 120 may facilitate the unlocking of the locking portion 112 from the locking position 122. For example, during an unlocking process as described below, an unlocking sleeve or an unlocking clamp may be used to squeeze the locking portion 112 within the locking position 122 (e.g., the locking window). In this case, with the guidance of the inclined surface, it may be easier for the unlocking sleeve or the unlocking clamp to arrive at the locking position 122 to perform the corresponding functions.

As shown in FIG. 14, the clip 110 may include two clip arms 111, and the proximal end of the clip arm 111 may form an elastic arm. The elastic arm may include a locking portion 112, and the locking portion 112 may include a locking convex. When the clip 110 is at the second position, the clip arms 111 may slidably bounce outward along the connecting pin 113, and the locking portion 112 may be locked with the locking position 122.

A side wall of the limiting tube 120 may include a locking window, and the locking window may form the locking position 122. When the clip 110 is at the second position, the locking portion 112 may extend into the locking position 122. When the locking portion 112 is pressed inward from the locking position 122, the locking portion 112 may be detached from the locking position 122, thereby the clip 110 may be unlocked.

Figure 2:
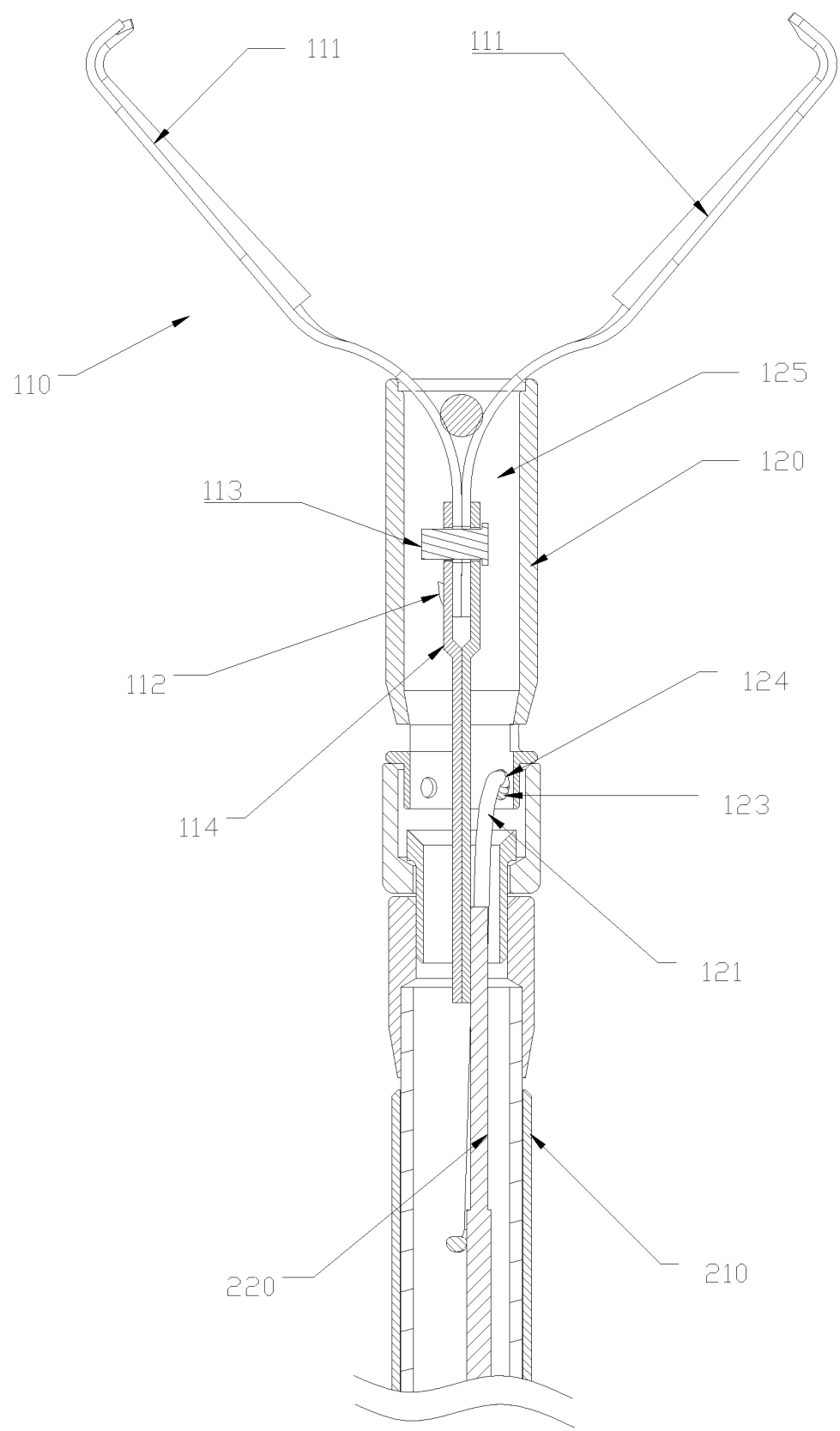
FIG. 2 is a schematic diagram illustrating a sectional view of a ligation device and a delivery portion according to embodiment one of the present disclosure.
Figure 3:
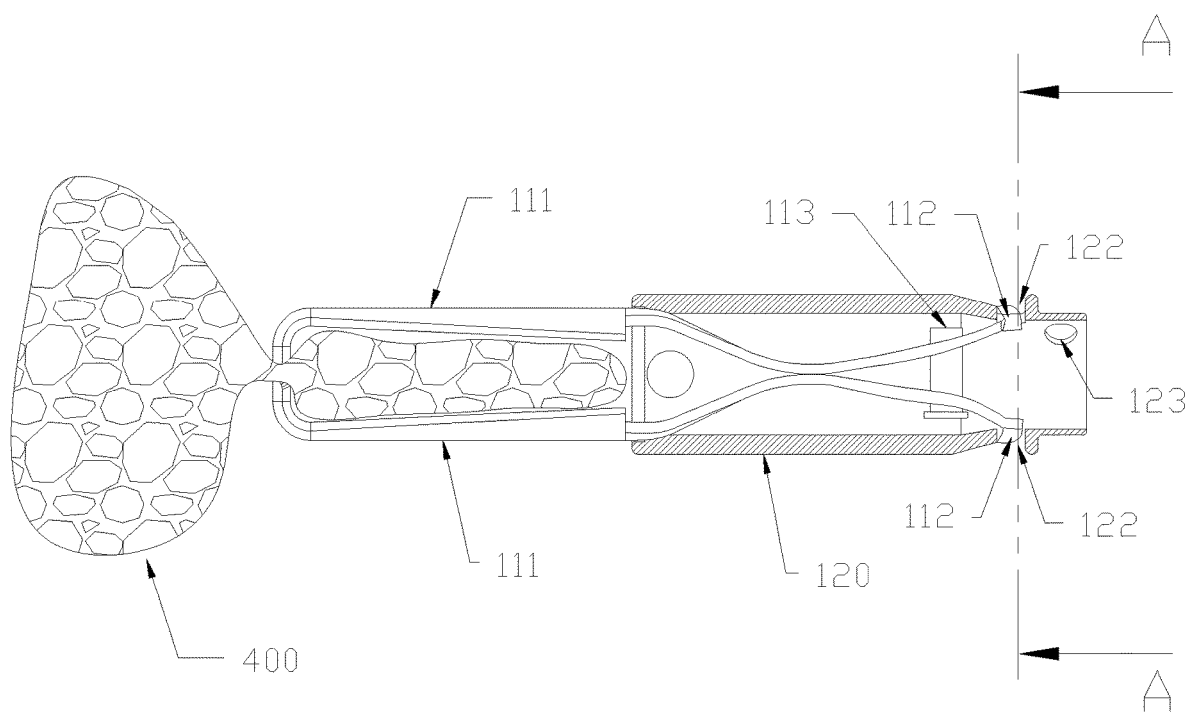
FIG. 3 is a first schematic diagram illustrating a ligation locking according to embodiment one of the present disclosure.
Figure 4:
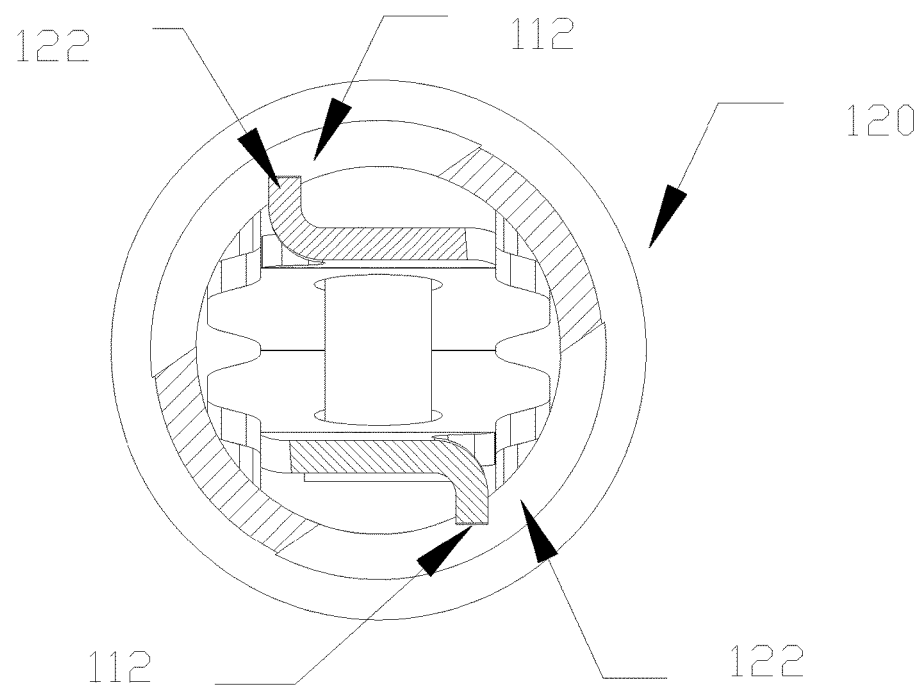
FIG. 4 is a schematic diagram illustrating an A-A section view of FIG. 3.
Figure 5:
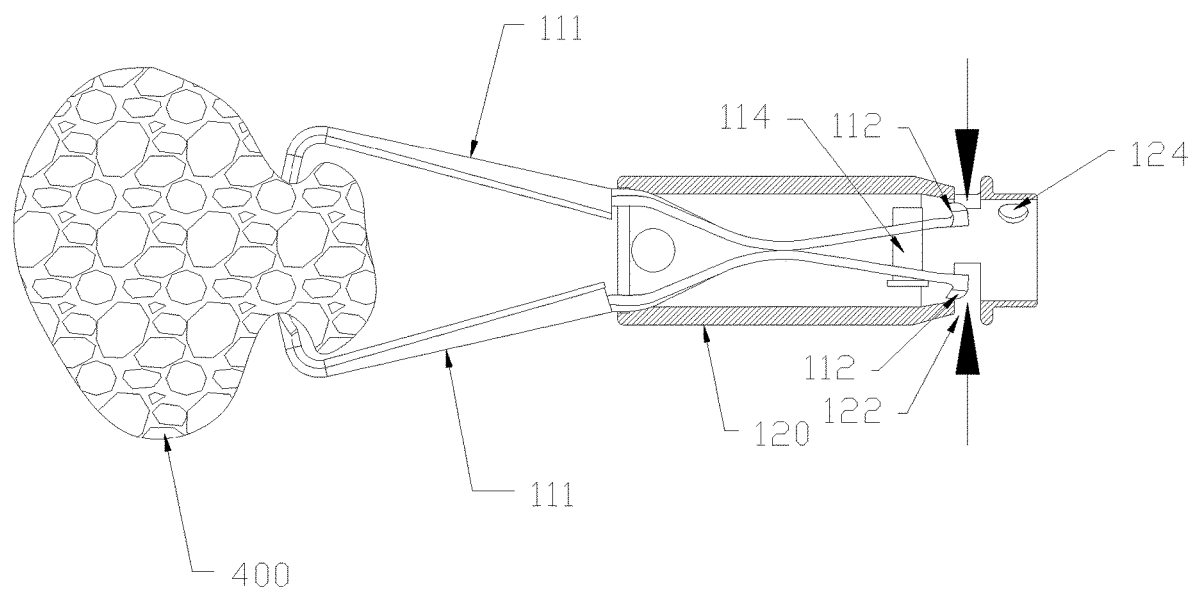
FIG. 5 is a schematic diagram illustrating an unlocking according to embodiment one of the present disclosure.

When ligating, the clip 110 may firstly be located at the first position, as shown in FIG. 1. The distal end of the clip 110 may be opened to clamp the tissue 400 of the ligating portion. Then the clip 110 may be moved toward the proximal end. By using the cooperation of the locking portion and the accommodation channel 125 of the limiting tube 120, when the clip 110 is moved from the first position to the second position, the proximal end of the clip arm 111 may automatically bounce outward. The locking portion 112 may be locked with the locking position 122, as shown in FIGS. 2 to 4. During the process of pulling the shaft, the shaft 220 may have been disconnected from the clip 110, and the sheath 210 may have been disconnected from the limiting tube 120 (It is not limited to this embodiment. In other embodiments, the shaft 220 may remain connected with the clip 110, or the sheath 210 may remain connected with the limiting tube 120). The location of the clip 110 in the limiting tube 120 may be locked, and the clip 110 cannot be detached from the distal end of the accommodation channel 125. The clip 110 may remain closed to ensure that the ligation is not released. After the clip 110 clamps the tissue 400 and the tissue 400 is ligated and locked, the tissue 400 may have a force to open the clip 110, thereby causing the clip 110 to move from the second position to the distal end. The clip 110 may be clamped by the locking between the locking portion 112 and the locking position 122 and the clip 110 may not be moved toward the distal end, thereby ensuring that the clip 110 is always in the ligated state.

Figure 8:
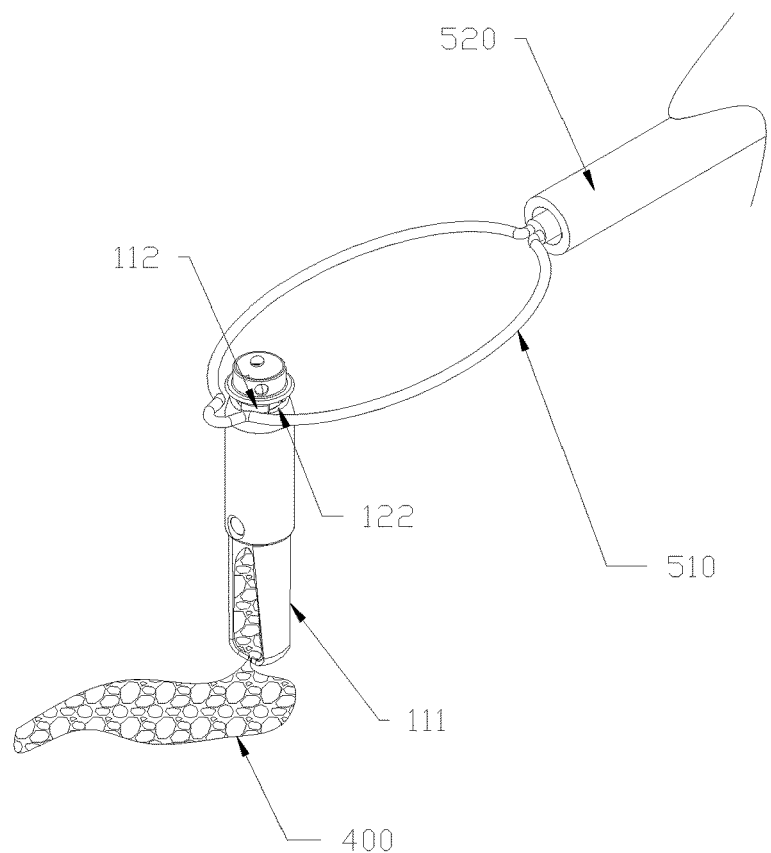
FIG. 8 is a schematic diagram illustrating a first operation of unlocking by using an unlocking sleeve according to embodiment one of the present disclosure.
Figure 9:
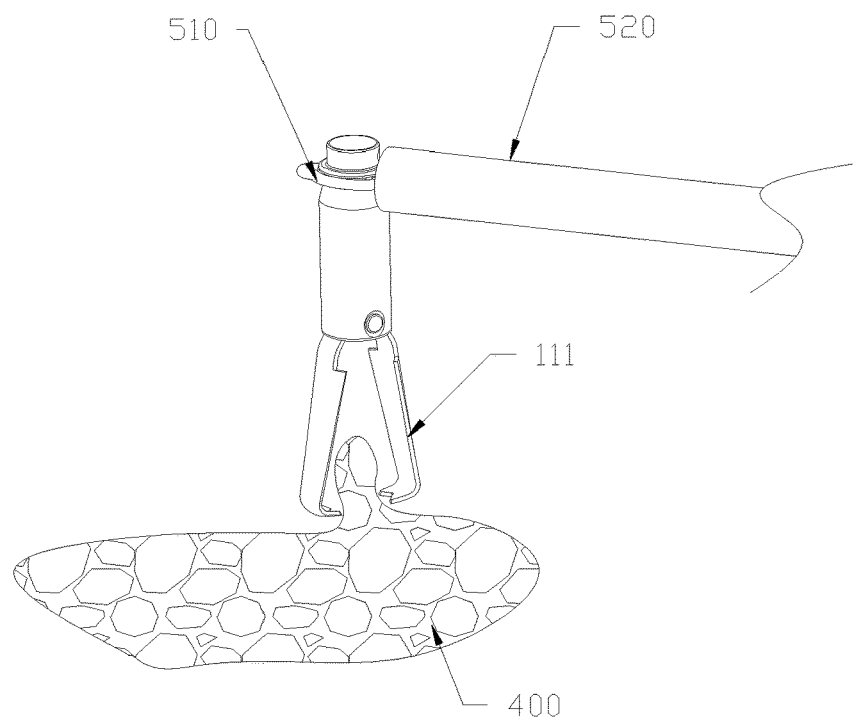
FIG. 9 is a schematic diagram illustrating a second operation of unlocking by using an unlocking sleeve according to embodiment one of the present disclosure.
Figure 10:
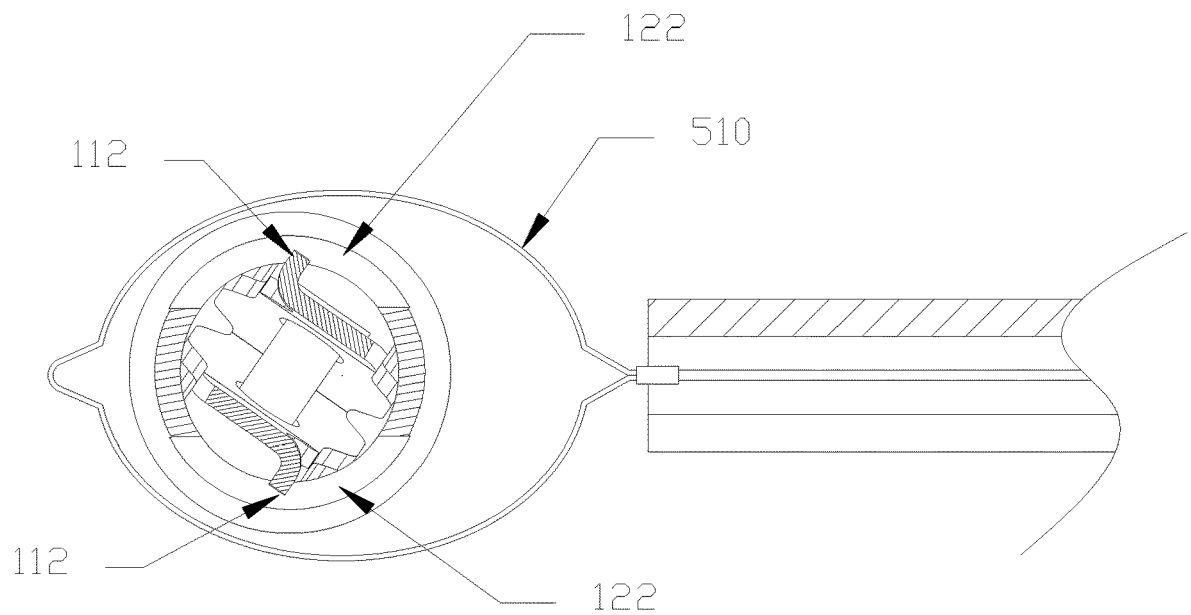
FIG. 10 is a schematic diagram illustrating a first structure of unlocking by using an unlocking sleeve according to embodiment one of the present disclosure.
Figure 11:
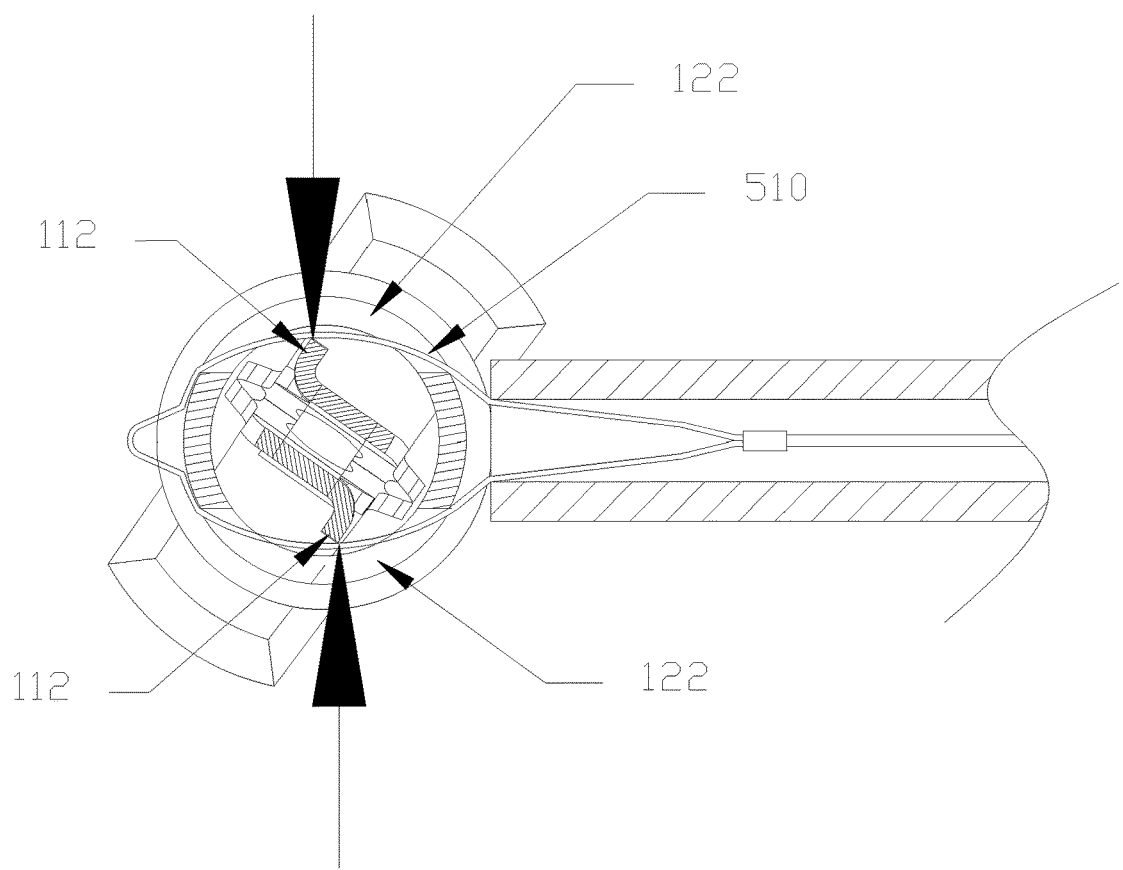
FIG. 11 is a schematic diagram illustrating a second structure of unlocking by using an unlocking sleeve according to embodiment one of the present disclosure.

After ligating, if it is necessary to open the clip 110 to release the ligated tissue 400, the locking portion 112 may be pressed inward, as shown in FIG. 5 and FIGS. 8 to 11, so that the locking portion may be detached from the locking position 122 and the locking portion may be unlocked from the locking position 122. At this time, the clip 110 may be unlocked from the limiting tube 120, and the locking portion may be pressed to re-enter into the accommodation channel 125. The clip 110 may be moved from the second position to the first position, and the distal end of the clip 110 may be re-opened to release the ligated tissue 400. During the process of releasing the ligated tissue 400, the ligated tissue 400 may be simply released by the clip 110 and not subjected to additional forces, which may not cause secondary damage to the tissue 400. As shown in FIGS. 8 to 11, the clip 110 may be unlocked by using an unlocking sleeve. The unlocking sleeve may include a snare 510, and a limiting device 520 connected with the snare 510. The snare 510 may match with the locking portion 112. When the unlocking is performed, the snare 510 may be sleeved on the locking portion 112, as shown in FIGS. 8 and 10. The limiting device 520 may be operated to tighten the snare 510 and the inner diameter of the snare 510 may be reduced. The snare 510 may press the locking portion 112 inwardly to unlock the locking portion 112 from the locking position 122, as shown in FIGS. 9 and 11.

In this embodiment, the unlocking may be performed directly by the snare 510 extending into the locking window (the locking position 122), and no additional unlocking portion, unlocking position, or unlocking window is required, however it is not excluded to provide additional unlocking portion, unlocking position, or unlocking window.

Embodiment Two

Figure 15:
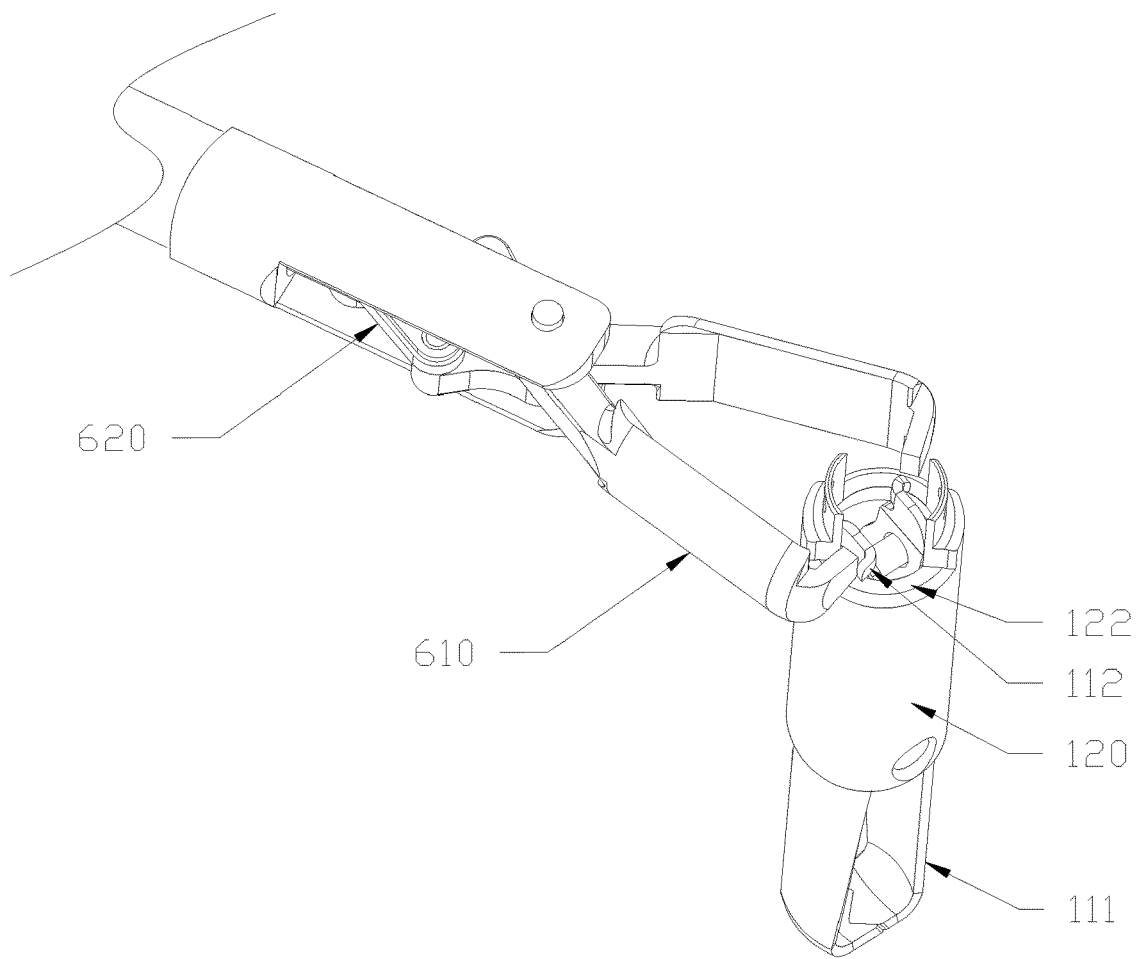
FIG. 15 is a schematic diagram illustrating an unlocking according to embodiment two of the present disclosure.
Figure 16:
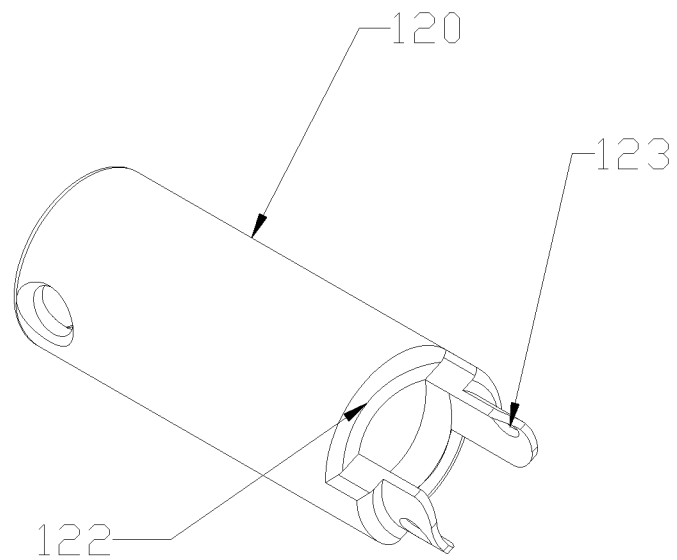
FIG. 16 is a schematic diagram illustrating a structure of a limiting tube according to embodiment two of the present disclosure.

Differences between embodiment two and embodiment one may include:

As shown in FIGS. 15 and 16, the vicinity of the proximal end and the proximal end of the limiting tube 120 may form the unlocking position. The locking portion 112 may be buckled with the proximal end of the limiting tube 120. In this way, the locking portion 112 may be directly exposed to the outside, and the locking portion 112 may be directly pressed inwardly by using the unlocking clamp to unlock the locking portion 112 from the locking position 122.

As shown in FIG. 15, the unlocking clamp may include a clamp arm 610, and an opening and closing device 620 connected with the clamp arm 610. The clamp arm 610 may match with the locking portion. When the unlocking is performed, the unlocking clamp may be sleeved on the locking portion 112. The opening and closing device 620 may be operated to close the clamp arm 610 and the clamp arm 610 may press the locking portion 112 inwardly to unlock the locking portion 112 from the locking position 122.

Embodiment Three

Figure 17:
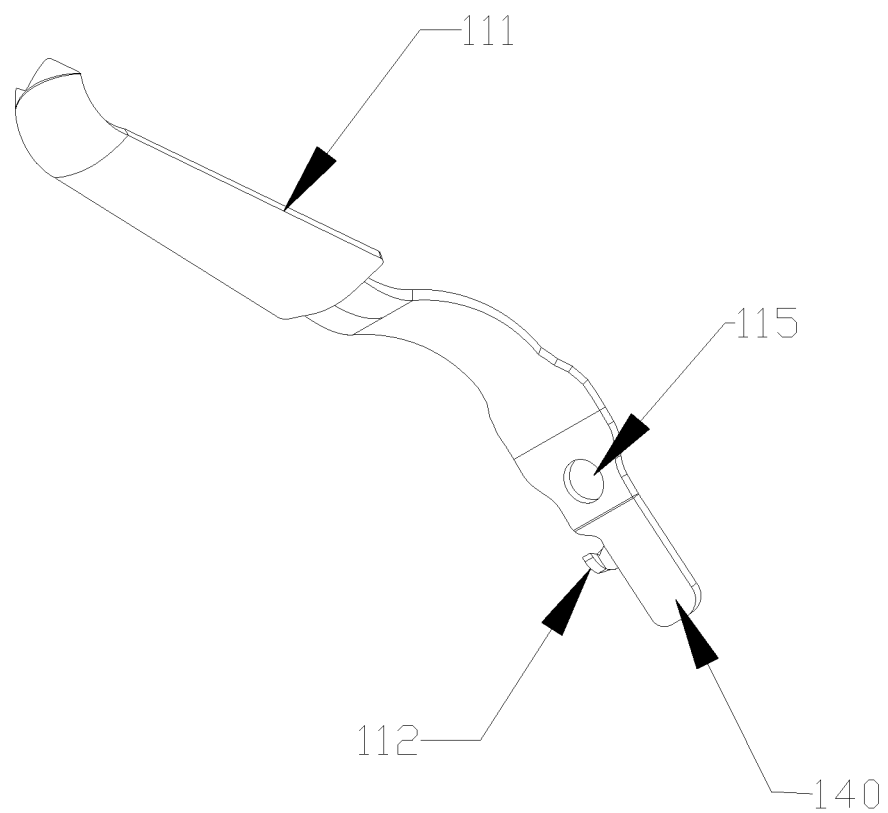
FIG. 17 is a schematic diagram illustrating a structure of a clip arm according to embodiment three of the present disclosure.
Figure 18:
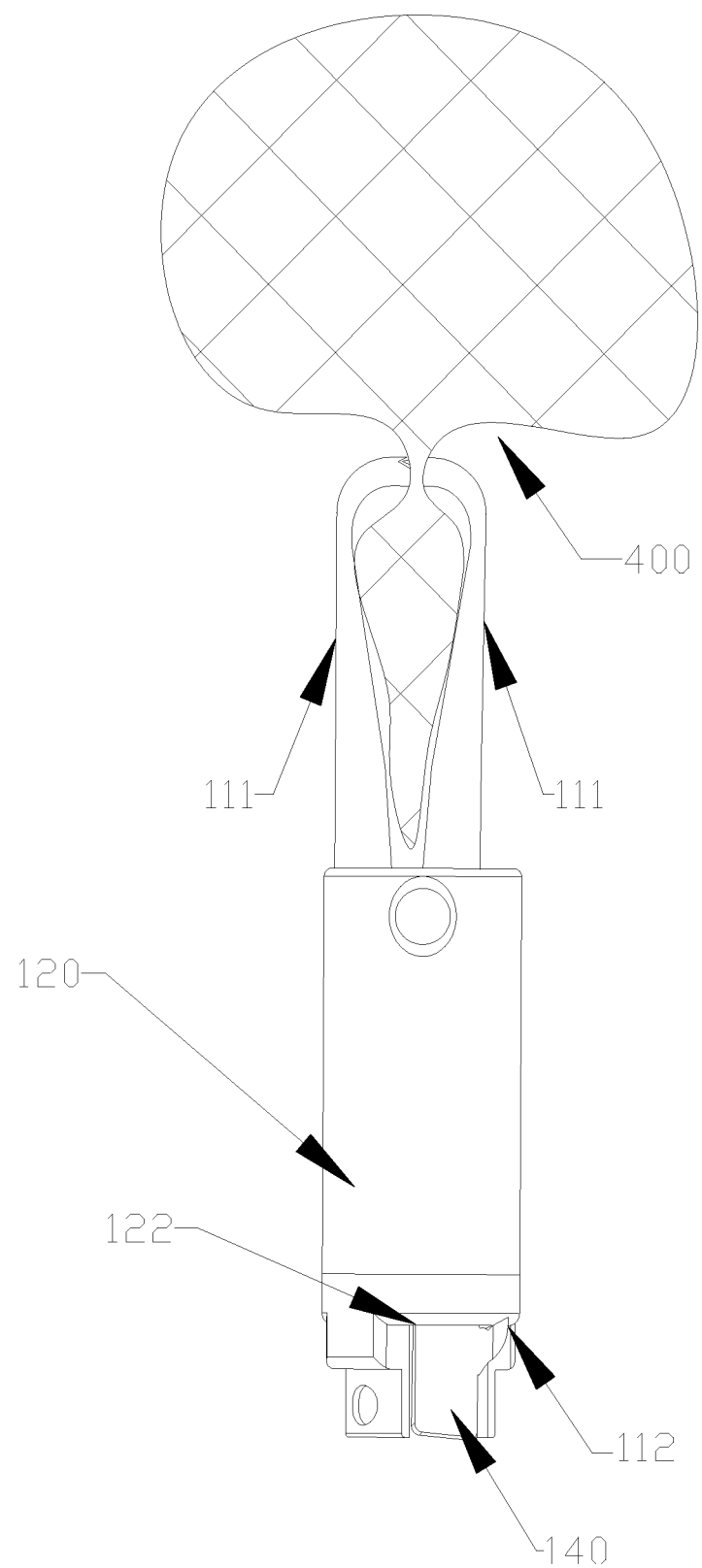
FIG. 18 is a schematic diagram illustrating a structure of a ligation locking according to embodiment three of the present disclosure.
Figure 19:
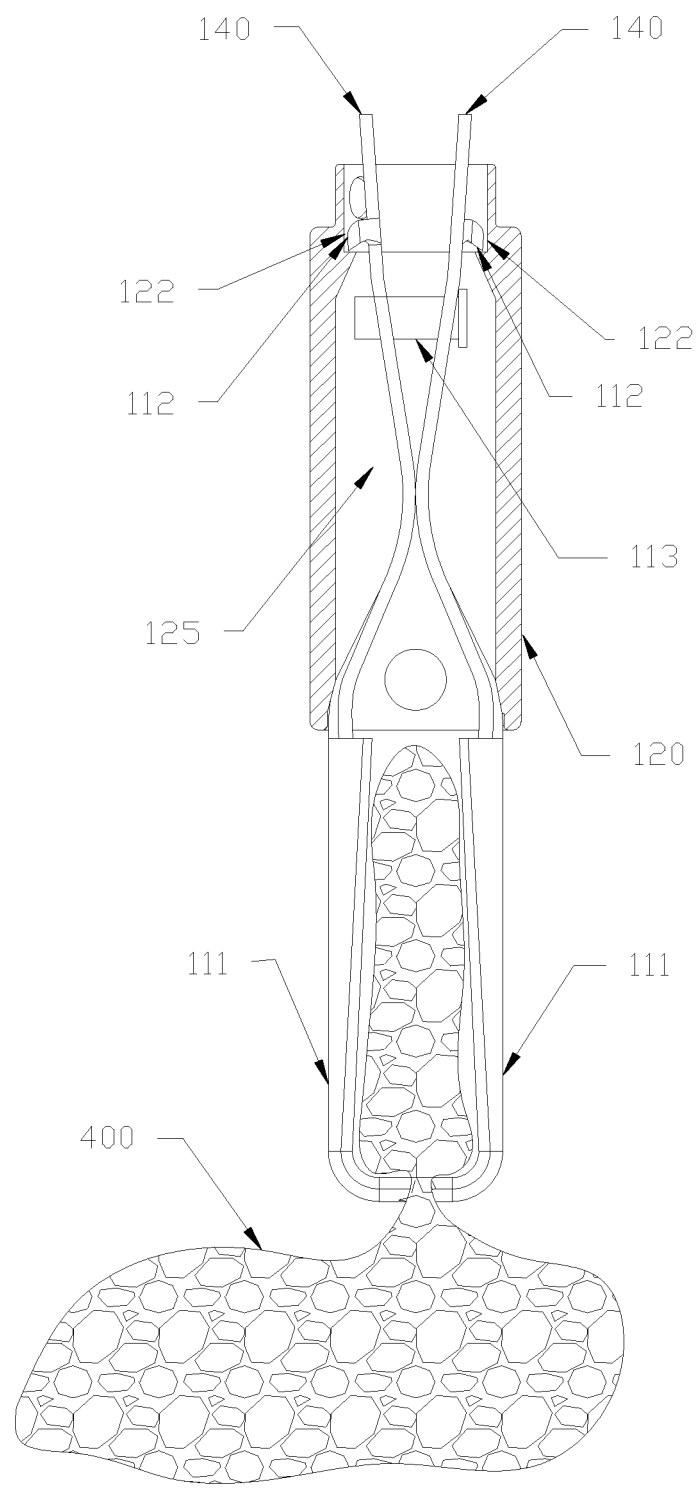
FIG. 19 is a schematic diagram illustrating a sectional view of a ligation locking according to embodiment three of the present disclosure.
Figure 20:
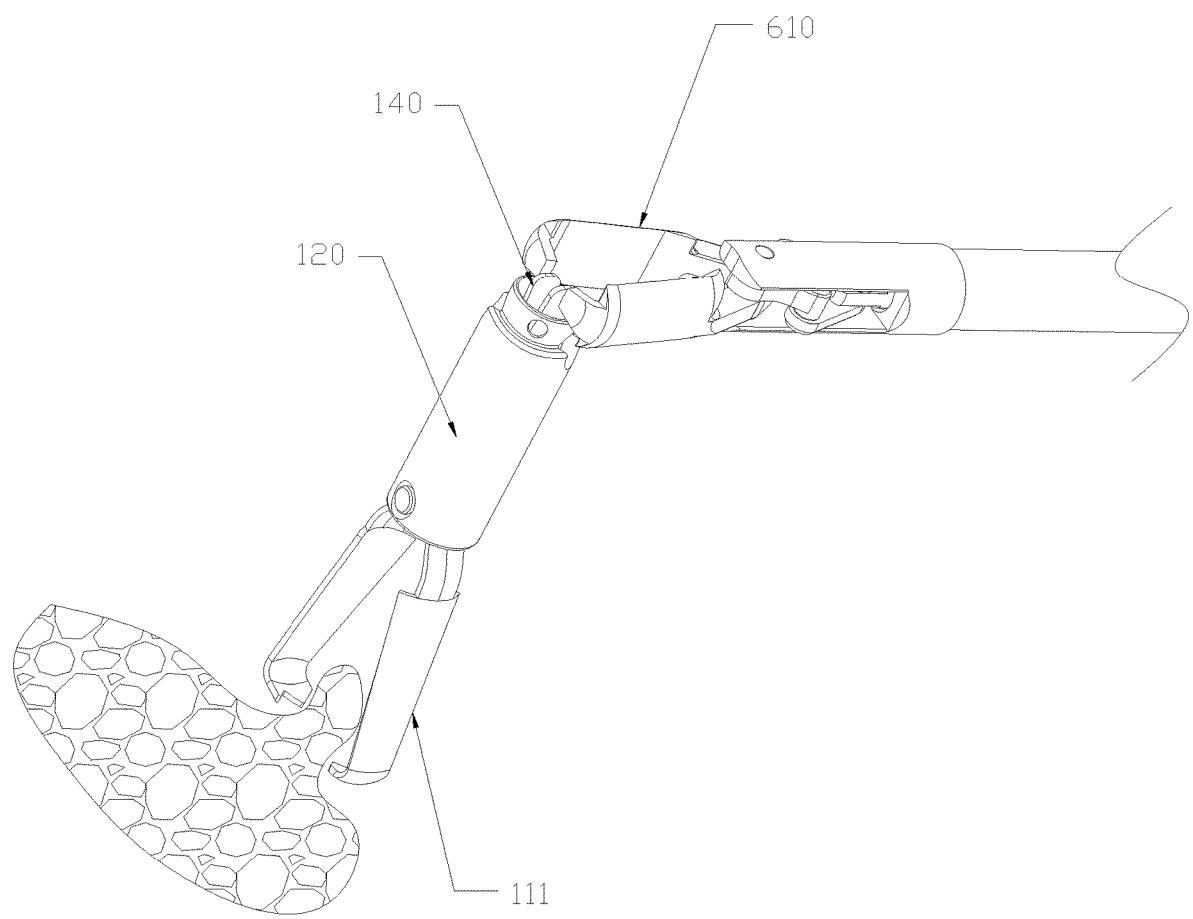
FIG. 20 is a schematic diagram illustrating an unlocking according to embodiment three of the present disclosure.

Differences between embodiment three and embodiment two may include:

As shown in FIG. 17, the proximal end of the clip arm 111 may include an unlocking portion 140. The unlocking portion 140 may be located at the proximal end of the locking portion 112. When the clip 110 is ligated and locked, as shown in FIGS. 18 and 19, the unlocking portion 140 may be located out of the accommodation channel 125 and directly exposed to the outside. The unlocking portion 140 may be pressed inwardly to unlock the locking portion 112 from the locking position 122. When the unlocking is performed, as shown in FIG. 20, the unlocking portion 140 may be directly pressed inward by using the unlocking clamp. The unlocking portion 140 may drive the locking portion 112 to move inward to unlock the locking portion 112 from the locking position 122.

Embodiment Four

Figure 21:
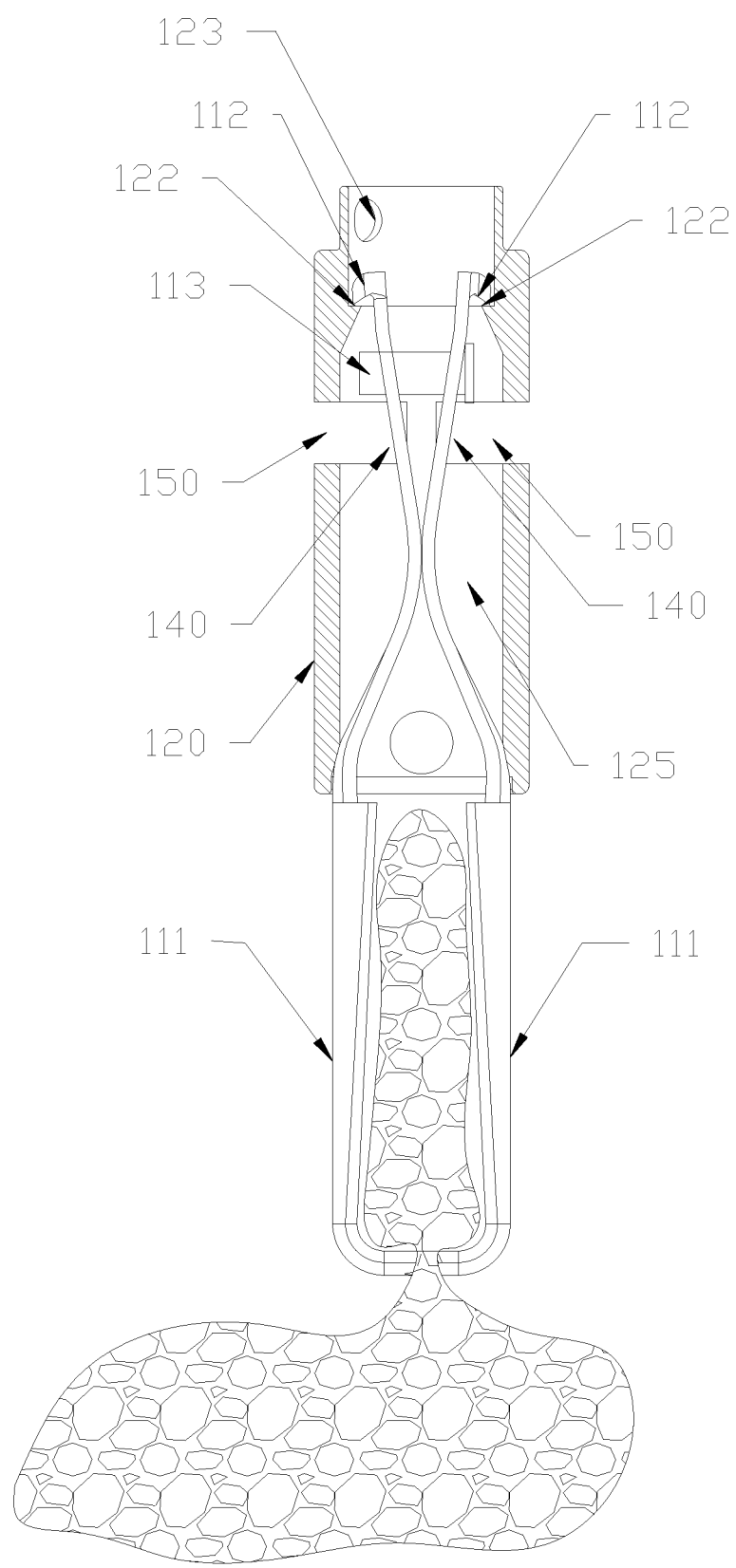
FIG. 21 is a schematic diagram illustrating a structure of a ligation locking according to embodiment four of the present disclosure.
Figure 22:
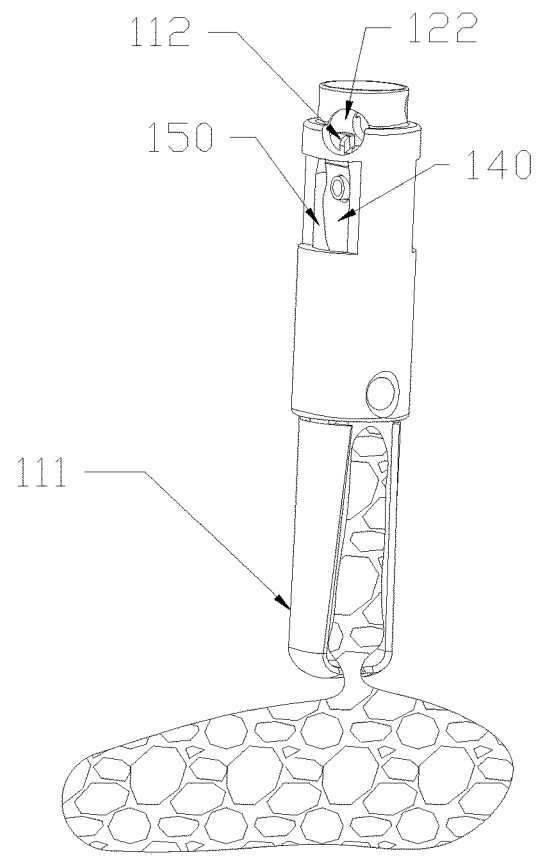
FIG. 22 is a schematic diagram illustrating a ligation locking according to embodiment four of the present disclosure.
Figure 23:
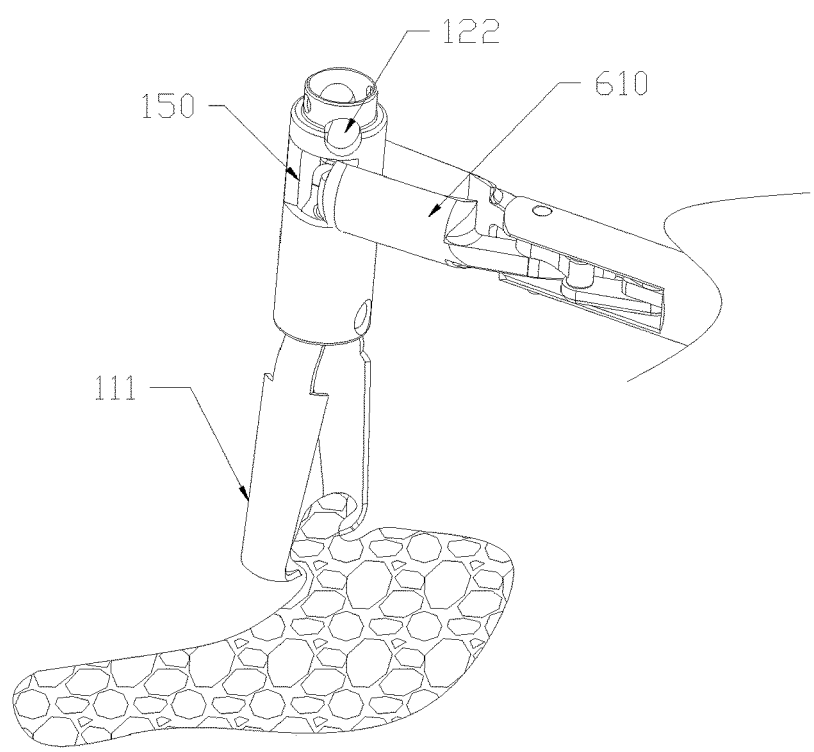
FIG. 23 is a schematic diagram illustrating an unlocking according to embodiment four of the present disclosure.

Differences between embodiment four and embodiment one may include:

As shown in FIG. 21, the proximal end of the clip arm 111 may include an unlocking portion 140. The unlocking portion 140 may be located at the distal end of the locking portion 112. A side wall of the limiting tube 120 may include an unlocking window 150. When the clip 110 is ligated and locked, as shown in FIG. 22, the unlocking window 150 may correspond to the unlocking portion 140. The unlocking portion 140 may be pressed through the unlocking window 150.

As shown in FIG. 21, the inner wall of the accommodation channel 125 may include a locking concave, and the locking concave may form the locking position 122. The locking concave (the locking position 122) may include a concave portion to buckle the locking portion 112. The locking concave is not limited to the form of a step structure as shown in FIG. 22, and can also be in the form of a groove, a blind hole, a through hole or other structures. When the clip 110 is ligated and locked, the locking portion 112 and the locking concave (the locking position 122) may be locked by buckling to each other.

As shown in FIG. 22, the clip may be unlocked by using an unlocking clamp. The unlocking portion 140 may be pressed by the unlocking clamp through the unlocking window 150. The unlocking portion 140 may drive the locking portion 112 to be detached and unlocked from the locking position 122.

Embodiment Five

Figure 24:
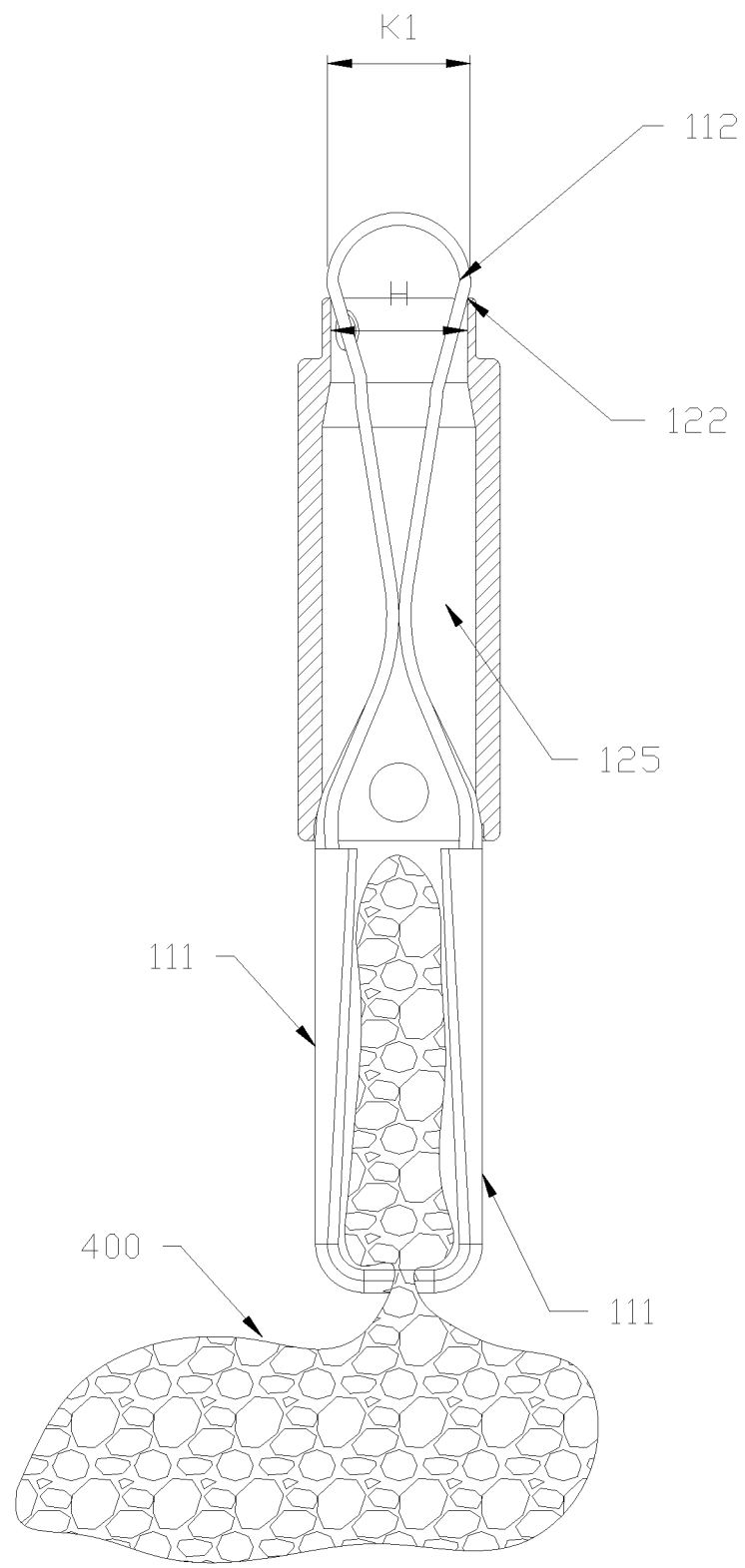
FIG. 24 is a schematic diagram illustrating a ligation locking according to embodiment five of the present disclosure.
Figure 25:
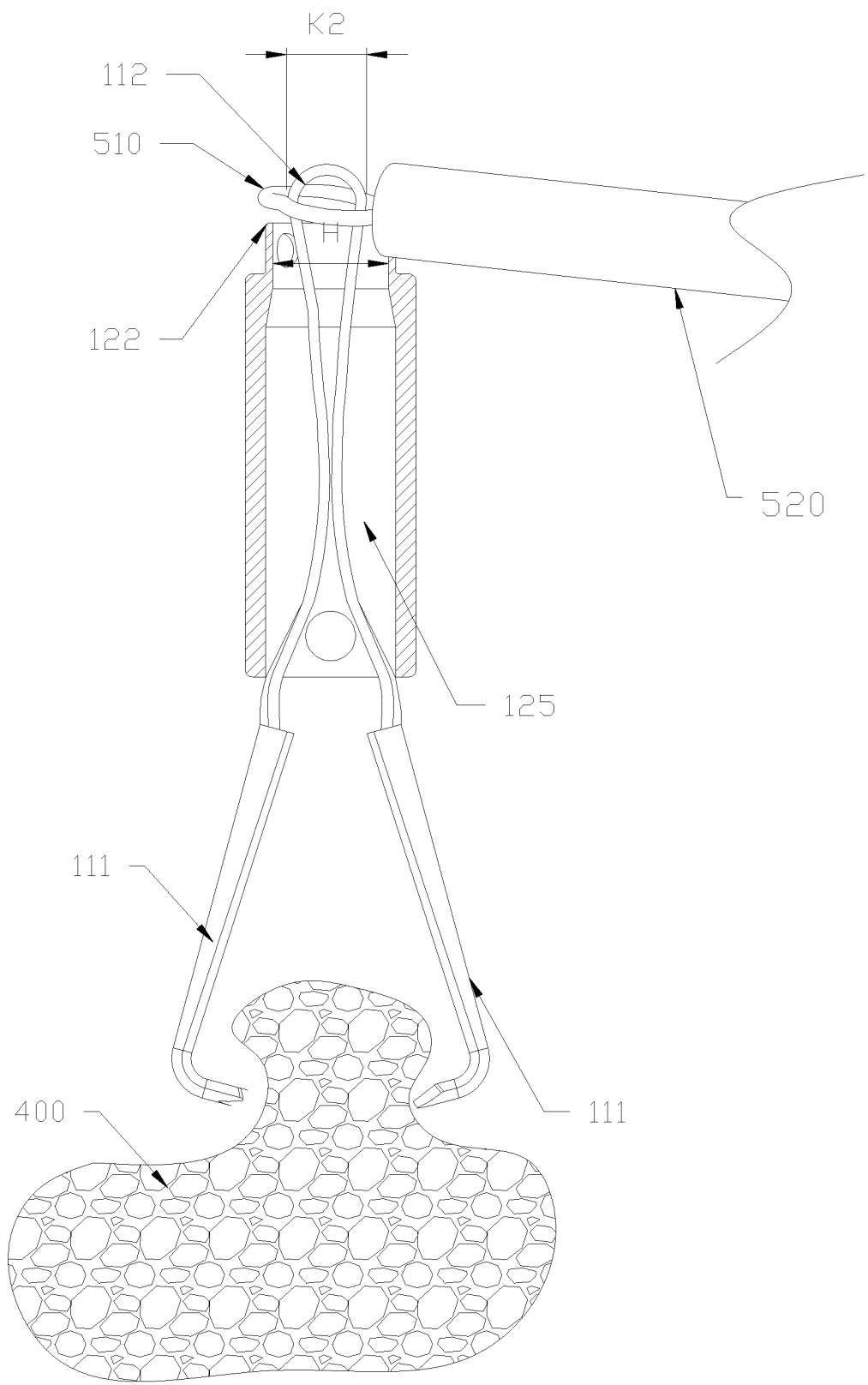
FIG. 25 is a schematic diagram illustrating an unlocking according to embodiment five of the present disclosure.

Differences between embodiment five and embodiment one may include:

As shown in FIGS. 24 and 25, the proximal ends of the two clip arms 111 may be connected, and the proximal ends of the two clip arms 111 may form a locking ring. The locking ring may include the locking portion 112. When the clip 110 is located at the second position, two sides or one side of the locking ring (the locking portion 112) may extend into the locking position 122, and the locking ring (the locking portion 112) may be locked with the locking position 122.

The vicinity of the proximal end and the proximal end of the limiting tube 120 may form the locking position 122. When the clip 110 is located at the first position, the locking ring may be squeezed into the accommodation channel 125, and the distal end of the clip 110 is opened. When the clip 110 is located at the second position, the locking ring (the locking portion 112) may be at least partially located outside the accommodation channel 125. The width K1 of the locking ring (the locking portion 112) may be larger than the width H of the accommodation channel 125, and the locking ring may abut against the proximal end of the limiting tube 120. The locking ring may be caught by the proximal end of the accommodation channel 125 and cannot enter the accommodation channel 125. At this time, the positional relationship of the clip 110 and the limiting tube 120 may be locked, and the clip 110 may remain ligated and not be opened. When the unlocking is performed, the locking ring may be clamped inward, and the width of the locking ring (the locking portion 112) may be reduced to K2. The width K2 of the locking ring (the locking portion 112) may be smaller than the width H of the accommodation channel 125 such that the locking ring (the locking portion 112) may be unlocked from the locking position 122. The locking ring (the locking portion 112) may re-enter into the accommodation channel 125, and the clip 110 may release the ligated tissue 400. The locking ring may be locked by using the proximal end of the limiting tube 120, of which the structure is simple. After the clip 110 clamps the tissue 400, the tissue 400 may have a force to open the clip 110, thereby causing the clip 110 to move from the second position to the distal end. The locking ring (the locking portion 112) may be clamped by the end of the limiting tube 120, and the clip 110 may not move toward the distal end, thereby ensuring that the clip 110 is always in the ligated state.

It is not limited to this embodiment, the side wall of the limiting tube 120 may include a locking window, and the locking window may form the locking position 122. When the clip 110 is located at the first position, the locking ring may be squeezed into the accommodation channel 125, and the distal end of the clip 110 is opened. When the clip 110 is located at the second position, the locking ring may be clipped in the locking window. On this basis, when the locking ring is pressed inward through the locking window, the locking ring may be detached from the locking window. The locking window may provide an operable window through which the locking ring may be squeezed and unlocked. The locking window may include one or two or more locking windows. Preferably, the locking window may include two locking windows which are respectively corresponding to the two sides of the locking ring, and the two sides of the locking ring may be clipped in the locking windows. The side of the locking ring may or may not extend out of the locking window.

In the claims and the embodiments, any one of the same two ligation devices may be an unlocking clamp for unlocking the other one. In the claims and the embodiments, a ligation device may be unlocked by any other ligation device. At this time, the clip arm of the ligation device may correspond to the clamp arm of the unlocking clamp.

The above embodiments are merely illustrative of several embodiments of the present disclosure, and the description thereof is specific and detailed, but is not to be construed as limiting the scope of the invention. It should be noted that, for those skilled in the art, there are several variations and modifications that may be made to the present disclosure without departing from the present disclosure concept. Therefore, the scope of protection of the present disclosure patent shall be subject to the appended claims.

What is claimed is:

1. A ligation device, comprising:
an unlocking tool, and;
a clip and a limiting tube, a distal end of the clip being used for ligation, the limiting tube having an accommodation channel, a proximal end of the clip being movable relative to the accommodation channel, the clip having a locking portion, the limiting tube being provided with a locking position, and the locking portion being matched with the locking position, wherein:
when the locking portion is being locked with the locking position, the locking portion can be unlocked from the locking position by pressing the locking portion using the unlocking tool; or, the clip is further provided with an unlocking portion that is coupled with the locking portion, and the locking portion can be unlocked from the locking position by pressing the unlocking portion using the unlocking tool; wherein the unlocking tool includes an unlocking sleeve or unlocking clamp, and the unlocking sleeve or unlocking clamp is configured to press the locking portion or the unlocking portion inwardly to unlock the locking portion from the locking position.

2. The ligation device of claim 1, wherein the locking portion is an elastic lock, and when the elastic lock is locked with the locking position, the elastic lock is locked with the locking position by bouncing outward from the accommodation channel.

3. The ligation device of claim 1, wherein:
the clip includes two clip arms, the proximal ends of the two clip arms are connected, and the proximal ends of the two clip arms form a locking ring that includes the locking portion; and
when the locking ring is locked with the locking position, at least part of the locking ring extends into the locking position.

4. The ligation device of claim 3, wherein the unlocking portion is located at a proximal end of the locking ring.

5. The ligation device of claim 3, wherein the unlocking portion is located at a distal end of the locking ring.

6. The ligation device of claim 1, wherein the clip includes an elastic arm, the elastic arm is provided with a locking convex that forms the locking portion.

7. The ligation device of claim 6, wherein the clip includes a clip arm, and a proximal end of the clip arm forms the elastic arm.

8. The ligation device of claim 6, wherein the elastic arm is further provided with the unlocking portion, and the unlocking portion is located at a proximal end or a distal end of the locking convex.

9. The ligation device of claim 1, wherein:
a proximal end of the limiting tube forms the locking position, and the locking portion is locked with the proximal end of the limiting tube via buckling.

10. The ligation device of claim 1, wherein a side wall of the limiting tube is provided with a locking window, and the locking window forms the locking position.

11. The ligation device of claim 10, wherein the locking portion can be unlocked from the locking window by operating the locking portion through the locking window.

12. The ligation device of claim 1, wherein:
an unlocking position is located at a vicinity of the proximal end of the limiting tube, and when the locking portion is locked with the locking position, the unlocking portion is located outside the proximal end of the accommodation channel.

13. The ligation device of claim 1, wherein the locking portion is unlocked from the locking position by operating the locking portion through the locking position.

14. The ligation device of claim 1, wherein when the clip is in a first position relative to the limiting tube, the distal end of the clip is opened, and the locking portion and the locking position are unlocked; and when the clip is in a second position relative to the limiting tube, the distal end of the clip is closed, and the locking portion is locked with the locking position.

15. The ligation device of claim 1, wherein:
an inner wall of the accommodation channel is provided with a locking concave, the locking concave forming the locking position, the locking portion extending into the locking concave such that the locking portion is locked with the locking concave.

16. The ligation device of claim 1, wherein:
a side wall of the limiting tube is provided with an unlocking window, and the locking portion can be unlocked from the locking position by operating the locking portion through the unlocking window.

17. The ligation device of claim 1, wherein the limiting tube is provided with an unlocking position, and the locking portion is unlocked from the locking position by operating the locking portion through the unlocking position.

18. The ligation device of claim 1, comprising:
a delivery portion including a sheath and a shaft, the sheath being sleeved outside the shaft, the shaft being connected with the clip through a first releasing portion, and the shaft being operated to drive the clip to move relative to the limiting tube, wherein
when the shaft is pulled to a first releasing condition, the first releasing portion separates the shaft from the clip.

19. The ligation device of claim 1, wherein the limiting tube has an inclined surface formed at a vicinity of the locking position, the inclined surface inclining toward a center of the limiting tube along a distal direction.

* * * * *